US006399339B1

(12) United States Patent
Wolberg et al.

(10) Patent No.: US 6,399,339 B1
(45) Date of Patent: Jun. 4, 2002

(54) METHOD FOR THE ENANTIOSELECTIVE REDUCTION OF 3,5-DIOXOCARBOXYLIC ACIDS, THEIR SALTS AND THEIR ESTERS

(75) Inventors: Michael Wolberg; Michael Müller, both of Jülich; Werner Hummel, Titz, all of (DE)

(73) Assignee: Forschungszentrum Julich GmbH (DE)

( * ) Notice: Subject to any disclaimer, the term of this patent is extended or adjusted under 35 U.S.C. 154(b) by 0 days.

(21) Appl. No.: 09/857,298

(22) PCT Filed: Aug. 12, 1999

(86) PCT No.: PCT/DE99/03971

§ 371 (c)(1),
(2), (4) Date: Jul. 10, 2001

(87) PCT Pub. No.: WO00/36134

PCT Pub. Date: Jun. 22, 2000

(30) Foreign Application Priority Data

Dec. 14, 1998 (DE) .......................................... 198 57 302

(51) Int. Cl.⁷ ............................ C12P 41/00; C12P 7/42; C12P 7/40; C12P 7/62
(52) U.S. Cl. ..................... 435/126; 435/134; 435/135; 435/136; 435/146; 435/190; 435/280
(58) Field of Search .................. 435/135, 190, 435/280, 134, 126, 146, 136

(56) References Cited

U.S. PATENT DOCUMENTS 6,037,158 A    3/2000   Hummel et al. ............ 435/190

FOREIGN PATENT DOCUMENTS

| DE | 196 10 984 | 9/1997 |
| EP | 0569998 | 11/1993 |
| WO | 97/00968 | 1/1997 |

OTHER PUBLICATIONS

Peters, J., et al, "Studies on the distribution and regulation of microbial keto ester reductases," *Applied Microbiology and Biotechnology* 38; 334–340, XP–0002134909 (1992).

Patel, R. N., et al, "Enantioselective microbial reduction of 3, 5–dioxo–6–(benzyloxy)hexanoic acid, ethyl ester," *Enzyme Microb. Technol. 15*: 1014–1021. XP–000651790 (1993).

*Primary Examiner*—Herbert J. Lilling
(74) *Attorney, Agent, or Firm*—Connolly Bove Lodge & Hutz LLP

(57) ABSTRACT

The invention relates to a method for the enantioselective reduction of 3,5-dioxocarboxylic acid derivatives and their syntheses. According to the invention, compounds of formula (4) are reacted with an alcohol dehydrogenase which preferably stems from *Lactobacillus brevis* and which is recombinantly over-expressed in *Escherichia coli*, in the presence of NADPH. The keto group in position 5 is enantioselectively reduced during this reaction. The keto group in position 3 can also be specifically syn- or anti-reduced in a further step by means of chemical or enzymatic reactions.

16 Claims, No Drawings

METHOD FOR THE ENANTIOSELECTIVE REDUCTION OF 3,5-DIOXOCARBOXYLIC ACIDS, THEIR SALTS AND THEIR ESTERS

The present invention relates to a method for the enantioselective reduction of 3,5-dioxo-carboxylic acids, their salts and their esters.

Homochiral 3,5-dihydroxycarboxylic acid derivatives having Formula 1 are intermediates in the synthesis of numerous natural and active substances.

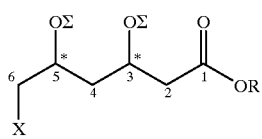

Formula 1 wherein X stands for a component from the group consisting of hydrogen, halogen, alkyl, aryl, CH=CHR², C≡CR³, (wherein R²=R, except for metal cation, and R³=R); Σ stands for H or for a protective group for the hydroxyl function; R stands for H, metal cation, for an alkyl, aryl, aralkyl or cycloalkyl radical.

Depending on the absolute configuration at the stereo centers C-3 and C-5, they can be systematically employed in the synthesis of chiral natural substances, such as mevic acids, or synthetic HMG-CoA-reductase inhibitors.

Other natural or active substances call for different configurations of the stereogenic centers in position C-3 and C-5. Consequently, there is great interest in the preparation of all possible stereoisomers of 3,5-dihydroxycarboxylic acid derivatives according to Formula 1 in an optically pure form. An advantageous method for the preparation of these compounds is the catalytic enantioselective reduction of the prochiral 3,5-dioxocarboxylic acid derivatives according to Formula 2.

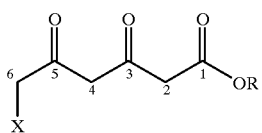

Formula 2

When this method is employed, there is no need for costly and environmentally burdensome separation procedures for the racemate, scalemate or diastereomer. This avoids the binding and cleavage of a stoichiometric quantity of a homochiral auxiliary group that are necessary in a diastereoselective synthesis. Moreover, the carbon skeleton of the 3,5-di-hydroxycarboxylic acid ester according to Formula 1 is already complete in the initial compounds according to Formula 2, that is to say, the stereocenters are only introduced into the overall synthesis sequence at a later point in time, as a result of which the loss of homochiral material is kept low.

European Patent Application No. 0,569,998 A2 discloses an enantioselective microbial process to reduce di-ketoesters that are oxyalkyl-substituted and oxyaralkyl-substituted in position 6.

WO 97/00968 discloses a process to reduce 3-oxo-5-hydroxy-carboxylic acid esters by means of reductases of Beauveria, Candida, Kluyveromycis, Torulaspora or Pichia.

DE 196 10 984 A1 discloses a stable microbial enzyme with alcohol-dehydrogenase activity, a process to obtain it as well as its use for the enantioselective reduction/oxidation of organic keto compounds/hydroxy compounds whereby, depending on the type of initial compounds, either R-hydroxy or S-hydroxy compounds are obtained.

The publication titled "Enantioselective microbial reduction of 3,5-dioxo-6-(benzyloxyl)hexanoic acid ethyl ester" in Enzyme Microb. Technol. (1993), 15 (12), 1014-21 ff. shows the reduction of 3,5-dioxo-6-(benzyloxy)hexanoic acid ethyl ester by means of a reductase.

As far as the terminology is concerned, a definition of the term will be introduced here as a working term that is to be valid within the disclosure:

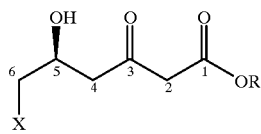

Formula 3

In Formula 3, the OH group projects from the paper plane in position 5, whereas the chains with the carboxylic acid function or with the ester function as well as with the radical X lie in the paper plane. Therefore, the hydrogen atom on C-5 recedes behind the paper plane. In accordance with the CIP (RS) nomenclature, as a function of the priority of the chain that is substituted with X, an R-designation or an S-designation would be employed for the same spatial configuration of the OH group projecting from the paper plane towards the front. As defined by the invention, the designation r-configuration will be used for an arrangement of the substituent used in which the OH group in position 5 projects forward from the paper plane, in which the hydrogen atom in position 5 extends below the paper plane and in which the side chain provided with the carboxylic acid function or with the ester function lies on the right-hand side of the fifth carbon atom while the side chain provided with the substituent X lies on the left-hand side of the fifth carbon atom. For those cases where the right-hand side chain provided with the carboxylic acid function or with the ester function has a higher priority than the left-hand side chain provided with the substituent X, this corresponds to the classic R-configuration. If the priorities of the above-mentioned chains are reversed (for example, by selecting X=halogen), then the classic S-configuration would be ascribed to the target compound. Both cases, however, should be encompassed by the definition of an r-configuration.

The objective of the invention is to regioselectively introduce an r-configuration of the hydroxyl group in position 5 during the enzymatic reduction of 3,5-dioxocarboxylic acid derivatives.

Another object of the invention is to provide a new method for preparing enantiomerpure 3,5-dihydroxycarboxylic acid derivatives, in other words, to create a process with which a syn-reduction or an anti-reduction of the keto group can systematically take place in position 3 towards position 5, so that the 3,5-dihydroxycarboxylic acid derivative has a tailor-made, absolute configuration with respect to C-3 which can be prepared as desired.

Another objective of the invention is to create an improved method for the synthesis of 3,5-dioxocarboxylic acid esters according to Formula 4 that can be used as educts for the enzymatic reduction.

On the basis of the generic part of claim 1, the objective is achieved according to the invention by means of the features indicated in the characterizing part of claim 1.

With the method according to the invention, it is now possible to reduce 3,5-dioxo carboxylic acids as well as their esters in a highly enantioselective manner and thus to obtain compounds that can then be employed in a synthesis of natural and active substances that have a defined absolute configuration in the 3,5-dihydroxycarboxylic acid structural element.

Advantageous embodiments of the invention are described in the subordinate claims.

The invention will be described below in a general manner.

According to the invention, a compound according to Formula 4

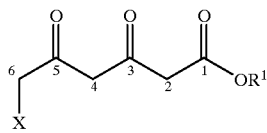

Formula 4 wherein $R^1$ stands for a component from the group consisting of alkyl, alkenyl, cyclo-alkyl, cycloalkenyl, aryl, aralkyl, cycloalkylalkyl, hydrogen or metal cation, and X stands for a component from the group consisting of hydrogen, halogen, alkyl, aryl, CH=CHR$^2$, C≡CR$^3$ (wherein $R^2=R^1$, except for metal cation, and $R^3=R^1$) is reacted by means of an alcohol dehydrogenase with the addition of NADPH or of another co-factor.

The term alkyl refers to straight-chain as well as to branched saturated carbon chains. Examples of these are methyl, ethyl, n-propyl, i-propyl, t-butyl, pentyl, i-pentyl, n-hexyl, i-hexyl. The term alkenyl relates to straight-chain and branched unsaturated hydro-carbons, examples of which are vinyl, 1-propenyl, allyl, butenyl, i-butenyl. The term cycloalkyl encompasses saturated, ring-shaped hydrocarbon chains consisting of three, four, five, six or seven carbon atoms. Cycloalkenyl designates unsaturated, ring-shaped hydrocarbons having 5, 6, 7 or 8 carbon atoms. Aryl refers to aromatic systems, enclosed heteroaromatic compounds and substituted aromatic systems, such as phenyl, p-tolyl, furanyl. Aralkyl refers to aryl radicals that are bonded via alkyl groups such as, for instance, a benzyl radical. The term cycloalkylalkyl comprises cycloalkyl radicals that are bonded via alkyl groups. Halogen preferably refers to fluorine and chlorine.

The alcohol dehydrogenase is preferably recombinant and stems from Lactobacillus, especially *Lactobacillus brevis* (recLBADH). The particularly advantageous aspect of this enzyme is that it can be recombinantly over-expressed and thus can be made available in large quantities. This also allows its use on a large, technical scale. The reaction can take place in an aqueous medium by means of an enzyme as well as on the intracellular level in a microorganism. In a preferred embodiment, recLBADH from *Lactobacillus brevis* which was recombinantly over-expressed in *Escherichia coli* is used. Another advantage of recLBADH is the capability of the enzyme to regenerate the necessary co-factor NADPH in a substrate-coupled manner, that is to say, NADPH does not have to be employed in a stoichiometric amount. Moreover, this avoids the need to add a second enzyme for purposes of regenerating the NADPH, which ultimately also reduces costs. With this transfer hydrogenation, an alcohol, preferably isopropanol, can serve as the hydrogen donor. The activity of recLBADH wan be increased by adding $Mg^{2+}$.

The method according to the invention can be carried out at room temperature since the enzyme recLBADH advantageously has a high heat stability. This also means that less enzyme is needed for a given yield, which translates into cost savings. Complex cooling measures can likewise be dispensed with. The method according to the invention, however, can also be conducted at the temperatures commonly employed for enzymatic reactions, between 0° C. and 70° C. [32° F. and 158° F.]. Preference is given to the range between 20° C. and 50° C. [68° F. and 122° F.].

The method according to the invention can be carried out at a pH value of 5.5, since the preferred enzyme displays a stability maximum at a pH of 5.5. This is advantageous since, at this pH value, many ester substrates according to Formula 4 exhibit a higher stability than at the higher pH values which normally have to be maintained in enzymatic reactions. The reaction, however, can also be carried out within a pH range from 5.5 to 9, preferably in the range between 5.5 and 6.5.

In order to ensure a suitable pH value, any buffer substance suitable for an enzymatic reaction can be used. Examples of these are triethanol amine (TEA), phosphate buffer or TRIS buffer. The concentration ranges for the buffers advantageously lie between 50 and 500 mmol/L.

The reaction product with the r-configuration is depicted in Formula 5, wherein the substituents $R^1$ and X have the same meaning as in Formula 4.

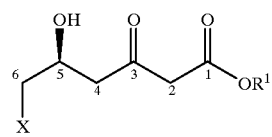

Formula 5

The enantiomer surpluses for these reactions can be said to be ≦98% to 100%.

In a refinement of the invention, the keto group of the compound in position 3 in Formula 5 is diastereoselectively reduced to form an OH group which is then in the syn-position or anti-position relative to the OH group in position 5.

The compound according to Formula 5 can be reacted to form the reaction product 6a, 6b employing methods that are known for the synthesis of syn-diols (6a) and anti-diols (6b).

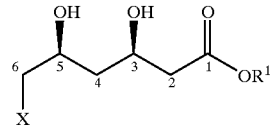

6a

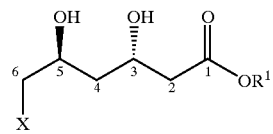

6b

For the production of syn-diols (6a) from β-hydroxy carbonyl compounds, these are, for example, sodium boron hydride reduction in the presence of trialkyl boranes or alkoxy-dialkyl boranes ([1] K. Narasaka, F. C. Pai, Tetrahedron 1984, 40, 2233–2238; [2] K. M. Chen, G. E. Hardtmann, K. Prasad, O. Repic, M. J. Shapiro, *Tetrahedron Lett.* 1987, 28, 155–158) while for the production of anti-diols (6b) from β-hydroxy carbonyl compounds, these are for example, reduction with tetramethyl ammonium triacetoxy boron hydride (D. A. Evans, K. T. Chapman, E. M. Carreira, *J. Am. Chem. Soc.* 1988, 110, 3560–3578).

Generally speaking, both chemical and enzymatic reductions are possible in the second step. The enzymatic reduction of position 3 can be carried out, for instance, with the following microorganisms or their isolated reductases: *Beauveria bassiana* ATCC 7159, *Candida humicola* CBS 1897, *Candida diddensiae* ATCC 20213, *Candida friedrichii* ATCC 22970, *Candida solani* CBS 1908, *Hansenula nonfementans* CBS 5764, *Kluyveromyces drosophilarum* CBS 2105, *Pichia angusta* NCYC 495, *Pichia angusta* NCYC R320, *Pichia angusta* NCYC R322, *Pichia haplophila* CBS 2028, *Pichia membranefaciens* DSM 70366, *Pichia pastoris* BPCC 260, *Pichia pastoris* BPCC 443, *Pichia pastoris* NCYC R321, *Torulaspora hansenii* ATCC 20220, *Candida pelliculosa* ATCC 2149, *Hansenula anomola* CBS 2230, *Neurospora crassa* ATCC 9277, *Pichia trehalophila* CBS 5361, *Mortierella alpina* MF 5534 (ATCC8979).

Other options are also the reductases from Saccharomyces, especially *Saccharomyces cerevisiae*, both in the cell as well as in isolated form.

The production method according to the invention can be advantageously carried out in a continuous process in an enzyme membrane reactor, as described, for example, in German Patent No. 39 37 892.

The enantioselective reduction of 3,5-dioxocarboxylic acid esters at position C-5 can take place with wild type enzymes and/or recombinant over-expressed enzymes as well as with whole cells. Preference, however, is given to extracellular reaction with a cell raw extract, since higher enantiomer surpluses are achieved.

In an advantageous embodiment of the invention, the substrate needed for the synthesis is prepared according to a method which, in contrast to other well-established methods for the synthesis of 3,5-dioxocarboxylic acid derivatives according to Formula 4, can make do with particularly inexpensive and simple initial materials. Another advantage of this method is its uncomplicated reaction engineering.

The method according to the invention will be described below by means of which high yields of 3,5-dioxocarboxylic acid esters according to Formula 2 can be obtained by acylating bisenolates according to Formula A, wherein $R^4$ stands for alkyl, alkenyl, cyclo-alkyl, cycloalkenyl, aryl, aralkyl, cycloalkylalkyl or metal cation

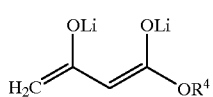

Formula A with easily available and inexpensive carboxylic acid esters according to Formula B, wherein X has the same meaning as in Formula 2 and wherein $R^5$ stands for an alkyl radical.

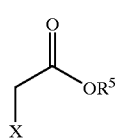

Formula B

According to known work methods, a bisenolate according to Formula A is made in situ on the basis of a β-ketoester with a lithium compound in an organic solvent. While the internal temperature of the reaction vessel is controlled, this bisenolate according to Formula A is then acylated by the addition of a carboxylic acid ester according to Formula B, whereby preference is given to the use of α-halogen carboxylic acid ester. Particularly preferred are the methyl esters of chloroacetic acid and of fluoroacetic acid. Subsequently, the mixture undergoes an acidic aqueous treatment in the presence of an organic solvent that is not miscible with water such as, for instance, acetic acid ethyl ester or diethyl ether.

The reaction according to the invention is preferably carried out in an inert-gas atmosphere under anhydrous conditions. An example of an inert gas is nitrogen or argon. Suitable solvents are inert organic solvents such as ethers, alkanes or cycloalkanes ($C_5$–$C_7$), toluene or benzene. Preference is given to aprotic coordinating solvents from the compound class of the ethers such as, for example, diethyl ether, dimethoxyethane or tetrahydrofuran (THF). THF is especially preferred.

The lithium compound is preferably highly alkaline, but not very nucleophilic. Preferred are lithium amides such as, for instance, lithium diisopropyl amide (LDA), lithium dicyclohexyl amide, lithium cyclohexyl isopropyl amide, lithium 2,2,6,6-tetramethyl piperidine (LiTMP) or lithium-bis-(trimethylsilyl)-amide (LiHMDS). LDA is particularly preferred. Other possibilities are organo-lithium compounds such as, for example, mesityl lithium or t-butyl lithium. The preferred molar ratio of lithium base to β-ketoester in order to produce the bisenolate ranges from 2:1 to 4:1, a molar ratio of 2.1:1 being particularly preferred.

The acylation of the bisenolate according to Formula B created in situ by means of the addition of a carboxylic acid ester according to Formula B is preferably done at an internal temperature of the reaction vessel ranging from −100° C. to +25° C. [−148° F. to +77° F.], at best between −80° C. and −40° C. [−112° F. to −40° F.]. Special preference is given to the range between −72° F. and −65° C. [−97.6° F. to −85° F.]. The molar ratio of carboxylic acid ester to bisenolate preferably lies between 0.5:1 and 2:1. Especially preferred is a ratio of 1:1.

The preparation of the highly alkaline reaction mixture preferably takes place two to 120 minutes after the addition of the last portion of carboxylic acid ester according to Formula B, at best after 15 to 30 minutes. For this purpose, the contents of the reaction vessel are poured into a cooled and vigorously stirred mixture consisting of an organic solvent that is not miscible with water, for example, acetic acid ethyl ester or diethyl ether, and an aqueous solution of an acid such as, for instance, diluted hydrochloric acid, acetic acid or ammonium chloride solution. In this context, preference is given to the use of bimolar hydrochloric acid and acetic acid ethyl ester.

In conjunction with the acylation of bisenolates according to Formula A with carboxylic acid esters according to Formula B, this approach constitutes an improvement over existing methods since a surplus of base or bisenolate is avoided and so is the use of special, expensive acylation reagents, catalysts or co-solvents. ([a] M. Yamaguchi, K. Shinato, H. Nakashima, T. Minami, *Tetrahedron* 1988, 44, 4767–4775; [b] N. S. Narasimhan, R. K. Ammanamanchi, *J. Org. Chem.* 1983, 48, 3945–3947; [c] S. N. Huckin, L. Weiler, *Can. J. Chem.* 1974, 52, 1343–1351). Another advantage is the uncomplicated reaction engineering since, unlike in Huckin et al., it is not necessary to add the components at alternating intervals, but rather, the necessary volumes can be added all at once. With the method according to the invention, no significant amount of by-products is formed. Various 3,5-dioxocarboxylic acid esters according to Formula 2 were prepared using the method according to the invention, examples of which are the compounds 6-chloro-3,5-dioxohexanoic acid-1,1-dimethyl ethyl ester and 6-fluoro-3,5-dioxohexanoic acid-1,1-dimethyl ethyl ester. Both compounds are new.

EXAMPLES

The method according to the invention will be presented below in the form of examples of preferred embodiments. However, the method according to the invention is not restricted to the examples.

Example 1

(3R, 5S)-6-Chloro-3,5-dihydroxyhexanoic acid-1,1-dimethyl Ethyl Ester a) 6-Chloro-3,5-dioxohexanoic acid-1,1-dimethyl Ethyl Ester

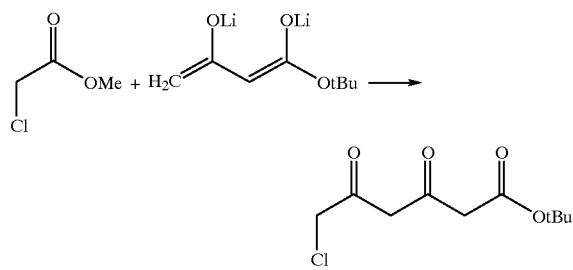

The following reaction is carried out in a heated standard glass apparatus (three-neck flask, drip funnel) in the absence of moisture and air ($N_2$ inert gas atmosphere). The apparatus is fitted with septa through which the reagents, all of which are commercially available, can be added by means of hollow needles in the absence of air. The temperature values indicated in the text refer to the internal temperature of the reaction vessel. Accordingly, the apparatus should be equipped with an inner thermometer. The reaction mixture is thoroughly stirred throughout the reaction (magnetic agitators).

Then 250 mL to 300 mL of absolutely anhydrous THF and 10.63 grams (105 mmol) of diisopropyl amine are placed into the apparatus described above. Once the flask contents have been cooled to −15° C. [5° F.] by means of a cooling bath containing ice and sodium chloride, 64 mL (approximately 105 mmol) of an n-butyl lithium solution in n-hexane (approximately 1.6 molar) are slowly dripped in under agitation via the drip funnel, during which process a temperature of 0° C. [32° F.] should not be exceeded. Once the addition has been completed, the flask remains in the cooling bath and the mixture is stirred for another 10 minutes, Subsequently, 7.91 grams (50 mmol) of 3-oxobutanoic acid-1,1-dimethyl ethyl ester are slowly dripped in, during which process a temperature of −5° C. [23° F.] should not be exceeded. After the addition has been completed, the flask is lifted slightly out of the cooling bath and the reaction mixture is stirred for another 10 minutes at −10° C. [14° F.] to a maximum of −5° C. [23° F.]. Afterwards, the cooling bath containing ice and sodium chloride is replaced by a cooling bath consisting of acetone, dry ice and some liquid nitrogen. After the reaction solution has cooled down to −72° C. [−97.6° F.], 5.43 grams (50 mmol) of chloroacetic acid methyl ester are added dropwise so slowly that a temperature of −65° C. [−85° F.] is not exceeded. After the addition has been completed, the reaction mixture is stirred for another 25 minutes at a temperature between −70° C. [−94° F.] and a maximum of −65° C. [−85° F.] and it is then poured into a mixture consisting of 150 mL of acetic acid ester and 150 mL of bimolar hydrochloric acid which has been vigorously stirred and cooled to 4° C. [39.2° F.] in an ice cooling bath. Immediately thereafter, the mixture is transferred to a separating funnel and thoroughly shaken. The phases are separated and the aqueous phase is extracted two more times with 50 mL of acetic acid ethyl ester each time. The combined organic phases are washed with 150 mL of $NaCHO_3$ solution (5%). If problems occur at this stage with the phase separation, then 40 grams of sodium chloride are dissolved into the mixture. The organic phase is subsequently washed with 150 mL of a saturated saline solution, dried with sodium sulfate, filtered and reduced to the greatest extent possible in a membrane pump vacuum of a rotation evaporator at a maximum temperature of 40° C. [104° F.]. Then 11 grams of an oily raw product (94%) remain which, according to an $^1$H-NMR analysis, consists of approximately 95% of the desired product. A thin-layer chromatogram (silica gel; ratio of acetic acid ethyl ester to i-hexane=3:7; development by means of quenching of fluorescence or evaporation with iodine) shows small fractions of polar and of nonpolar impurities.

The product can be purified by bulb tube distillation at a maximum temperature of 75° C. [167° F.] and at a vacuum of at least 0.01 mbar. In this manner, 0.83 grams of analytically pure product were isolated from 1.12 grams of the raw product. Alternatively, flash chromatography can be carried out with acid-washed, metal-free silica gel. Prior to the chromatography, commercially available silica gel (standard grade) is suspended for 24 hours in bimolar hydrochloric acid, filtered, washed with de-ionized water until the washing solution has a pH value of 5.5 and subsequently dried for at least 24 hours at 105° C. [221° F.] and at normal pressure. See also J. S. Hubbard, T. M. Harris, *J. Org. Chem.* 1981, 46, 2566–2570). With this method, 2.72 grams of analytically pure product and 0.24 grams of a mixed fraction were obtained from 3.81 grams of the raw product (column having a diameter of 6 cm., 220 grams of silica gel, ratio of acetic acid ethyl ester to i-hexane=2:8; 60-mL fractions). The compound can be stored for several months at −20° C. [−4° F.].

$^1$H-NMR (300 MHz, $CDCl_3$, 22° C. [71.6° F.]) 1) enol form δ: 14.76 (s, 1H, OH, br), 5.97 (s, 1H, H4), 4.06 (s, 2H, H6), 3.31 (s, 2H, H2), 1.48 (s, 9H, 3×$CH_3$). 2) ketoform δ: 4.21 (s, 2H, H6), 3.92 (s, 2H, H4), 3.49 (s, 2H, H2), 1.47 (s, 9H, 3×$CH_3$). keto: enol=12:88. $^{13}$C-NMR (75.5 MHz, $CDCl_3$, only the signals of the enol form are given) δ: 28.14 (C($CH_3$)$_3$), 44.35 (C6), 46.03 (C2), 82.56 (OC ($CH_3$)$_3$), 98.89 (C4), 166.48 (COOtBu), 187.05, 187.34 (C3, C5).

b) (S)-6-Chloro-5-hydroxy-3-oxohexanoic acid-1,1-dimethyl Ethyl Ester

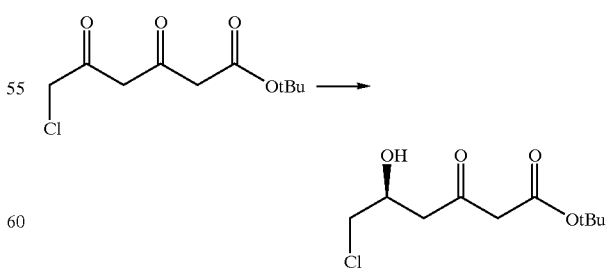

The following enzymatic reaction is carried out with the oxido-reductase recLBADH. A cell raw extract is produced by means of the wet grinding of moist cell matter of a recombinant *E. coli* strain (recADHHB101+). The cultivation conditions and the details of the cell digestion are described in the literature (B. Riebel, Dissertation, Heinrich-Heine University, Düsseldorf, Germany, 1996; also see German Patent Application No. 19610984,1, 1996). According to this method, approximately 3 mL of cell raw extract are obtained from 1 gram of moist cell matter. The activity of this enzyme preparation is about 1100 U/mL under the following conditions: photometric determination at 340 nm ($\epsilon_{NADPH}$=6.22 cm$^2$/μmol); substrate: acetophenone (10 mM), NADPH (0.25 mM), MgCl$_2$ (1 mM), phosphate buffer (100 mM, pH of 6.5), limiting enzyme quantity; 1 mL of the total volume; temperature: 25° C. [77° F.]; measurement over 1 minute. An enzyme unit (U) is defined at the enzyme quantity that oxidizes 1 μmol of NADPH per minute under the conditions indicated.

The reaction engineering will be described below in its simplest form (batch reactor, monophasic). A round flask of a suitable size serves as the reaction vessel. During the enzymatic reduction, the flask contents are slowly (approximately 60 rpm) stirred with a magnetic agitator.

A solution consisting of 2.21 grams (9.4 mmol) of the 6-chloro-3,5-dioxohexanoic acid-1,1-dimethyl ethyl ester produced in step a) in 5.66 grams (94 mmol) of isopropanol (for purposes of co-factor regeneration) is added to 470 mL of phosphate-citrate buffer (250 mM Na$_2$HPO$_4$, 125 mM citric acid, set to a pH of 5.5 with NaOH). A brief ultrasound treatment can be applied so as to accelerate the dissolving process. Moreover, 1.92 grams (9.4 mmol) of magnesium-chloride hexahydrate and 401 mg (0.47 mmol) of triphosphopyridine-neclectotide sodium salt (NADP$^+$, 90%, for instance, FLUKA No. 93210) are also added to this solution. The increased concentration of magnesium ions is intentional in this particular application example. Subsequently, the reaction is initiated by adding 1000 U (see above) of recLBADH and the reaction flask is sealed with a stopper. During the reaction, the temperature of the reaction solution is kept at 25° C. [77° F.]. After 16 hours, the flask contents are filtered and transferred into a separation funnel and extracted with 400 mL of acetic acid ethyl ester. In order to facilitate phase separation, 135 grams of sodium chloride are dissolved into the mixture. The phases are separated and the aqueous phase is extracted two more times with 400 mL of acetic acid ethyl ester each time. The combined organic phases are dried with sodium sulfate, filtered and reduced to the greatest extent possible in the membrane pump vacuum of a rotation evaporator at a maximum temperature of 40° C. [104° F.]. The yield is 1.97 grams of an oily raw product (88%) which, according to $^1$H-NMR, consists of at least 90% of the desired product. The nuclear-resonance spectrum reveals a small amount of a cyclization product (2-(t-butyl-oxycarbonyl)-methyl-3(2H)-furanone) as an impurity. The fraction of cyclization product rises when the reaction is carried out at higher pH values. The desired product is purified by means of flash chromatography (column having a diameter of 5 cm, 148 grams of silica gel, ratio of acetic acid ethyl ester to i-hexane=4:6; 50-mL fractions) and yields 1.67 grams of analytically pure product (75%) in addition to 0.16 grams of a mixed fraction with the above-mentioned cyclization product.

$^1$H-NMR (300 MHz, CDCl$_3$, 22° C. [71.6° F.], only the signals of the keto form are given) δ: 4.31 (m, 1H, CHOH), 3.62 (dd, J=11.2, 5.1 Hz, 1H, H6), 3.57 (dd, J=11.2, 5.0 Hz, 1H, H6), 3.41 (s, 2H, H2), 3.10 (s, 1H, OH, br), 2.90 (dd, J=17.5, 5.0 Hz, 1H, H4), 2.83 (dd, J=17.5, 7.3 Hz, 1H, H4), 1.47 (s, 9H, 3×CH$_3$). keto: enol=approximately 95:5. $^{13}$C-NMR (75.5 MHz, CDCl$_3$, only the signals of the keto form are given) δ: 28.13 (3×CH$_3$), 46.57 (C6), 48.43 (C4), 51.31 (C2), 67.58 (C5), 82.73 (OC (CH$_3$)$_3$), 166.22 (COOtBu), 202.93 (C3).

$[\alpha]_D^{25}$=−24.9 (CHCl$_3$, c=1.35)

The optical purity and the configuration are determined by comparing the specific rotation of the product with the specific rotation of the most enantiomer-pure possible sample of the same compound. For this purpose, an authentic sample of the product (S)-6-chloro-5-hydroxy-3-oxohexanoic acid-1,1-dimethyl ethyl ester is produced according to a known method (J. K. Thottathil, Y. Pendri, W. S. Li, D. R. Kronenthal, U.S. Pat. No. 5,278,313, 1994) using a commercially available enantiomer-pure compound ((S)-4-chloro-3-hydroxybutanoic acid ethyl ester, 96%, ALDRICH No. 460524, >97% ee (manufacturer's information), measured: $[\alpha]_D^{25}$=−21.7 (CHCl$_3$, c=2.33), literature: $[\alpha]_D^{21}$=+20.9 (CHCl$_3$, c=7.71), 97% ee, (R)-enantiomer (M. Kitamura, T. Ohkuma, H. Takaya, R. Noyuri, *Tetrahedron Lett.* 1988, 29, 1555–1556)). The raw product thus obtained is purified according to the method described above.

The $^1$H-spectrum and the $^{13}$C-spectrum of this comparative compound exactly match the data given above. The specific rotation of the purified authentic sample is the following:

$[\alpha]_D^{25}$=−23.0 (CHCl$_3$, c=1.52)

A comparison of the two specific rotations shows that the above-mentioned enzymatic reduction yields a product with extremely high optical purity. The matching of the sign of the specific rotation demonstrates that the product is present in the (S)-configuration.

c)(3R, 5S)-6-Chloro-3,5-dihydroxy hexanoic acid-1,1-dimethyl Ethyl Ester

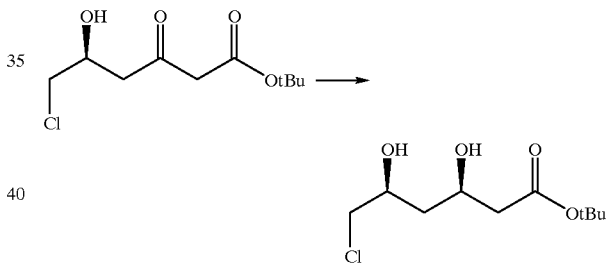

Starting with the raw product produced in step b), the desired target compound can be prepared by means of reduction with sodium boron hydride in the presence of diethyl methoxy borane. This process is described in the literature specifically for the application example at hand here (J. K. Thottathil, Y. Pendri, W. S. Li, D. R. Kronenthal, U.S. Pat. No. 5,278,313, 1994).

Example 2

(3R, 5R)-Dihydroxy hexanoic acid-1,1-dimethyl Ethyl Ester a) 3,5-Dioxohexanoic acid-1,1-dimethyl Ethyl Ester

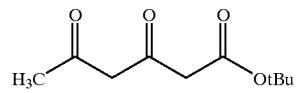

This prochiral initial compound is prepared by means of a method described in the literature, through alcoholysis and de-carboxylation of aceto-acetylated Meldrum's acid (F. Yuste, F. K. Brena, H. Barrlos, R. Sanchez-Obregon, B. Ortiz, F. Walls, *Synth. Commun.* 1988, 18, 735–739).

b)(R)-5-Hydroxy-3-oxohexanoic acid-1,1-dimethyl Ethyl Ester

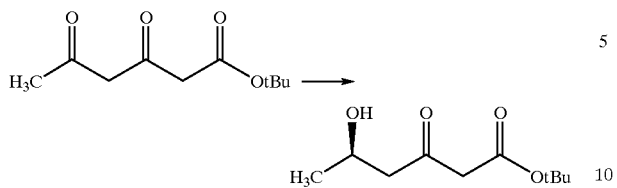

For this enzymatic reaction, a cell raw extract is used of the kind described in step b) of Example 1.

A solution consisting of 1.04 grams (5.17 mmol) of the 3,5-dioxohexanoic acid-1,1-dimethyl ethyl ester produced in step a) in 3.1 grams (52 mmol) of isopropanol (for purposes of co-factor regeneration) is added to 260 mL of phosphate buffer (125 mM $Na_2HPO_4$, 125 mM $Na_2H_2PO_4$, set to a pH of 6.6 with HCl). Moreover, 53 mg (0.26 mmol) of magnesium-chloride hexahydrate and 220 mg (0.26 mmol) of triphosphopyridine-nucleotide sodium salt ($NADP^+$, 90%, FLUKA No. 93210) are also added to this solution. Subsequently, the reaction is initiated by adding 215 U of recLBADH and the reaction flask is sealed with a stopper. The reaction solution is slowly (60 rpm) stirred with a magnetic agitator. During the reaction, the temperature of the reaction solution is kept at 25° C. [77° F.]. After 28 hours, the flask contents are filtered through a glass filter (pore size 4). The filtrate is transferred to a separation funnel and extracted with 150 mL of acetic acid ethyl ester. In order to facilitate phase separation, 75 grams of sodium chloride are dissolved into the mixture. The phases are separated and the aqueous phase is extracted two more times with 150 mL of acetic acid ethyl ester each time. The combined organic phases are dried with sodium sulfate, filtered and reduced to the greatest extent possible in the membrane pump vacuum of a rotation evaporator at a maximum temperature of 40° C. [104° F.]. The yield is 0.96 grams of an oily raw product (92%) which, according to $^1$H-NMR, consists of at least 90% of the desired product. The nuclear-resonance spectrum reveals a small amount of the educt as an impurity. The product can be purified by means of vacuum bulb-tube distillation (55° C. [131° F.]. 0.02 mbar) or else by means of flash chromatography. Using the latter method, 0.82 grams (78%) of the analytically pure product can be obtained (column having a diameter of 3 cm, 45 grams of silica gel, ratio of acetic acid ethyl ester to n-hexane=4:6; 20-mL fractions). The NMR data matches that of the literature (L. Shao, H. Kawano, M. Saburi, Y. Uchida, *Tetrahedron* 1993, 49, 1997–2010).

$^1$H-NMR (300 MHz, $CDCl_3$, 22° C. [71.6° F.], only the signals of the keto form are given) δ: 4.27 (m, 1H, CHOH), 3.38 (s, 2H, H2), 2.91 (s, 1H, OH, br), 2.74 (dd, J=17.7, 3.2 Hz, 1H, H4), 2.64 (dd, J=17.7, 8.5 Hz, 1H, H4), 1.48 (s, 9H, 3×$CH_3$), 1.21 (d, J=6.4 Hz, 3H, H6). keto: enol= approximately 95:5. $^{13}$C-NMR (75.5 MHz, $CDCl_3$, only the signals of the keto form are given) δ: 22.59 (C6), 28.13 (3×$CH_3$), 51.19, 51.29 (C2, C4), 63.93 (C5), 82.44 (OC$(CH_3)_3$), 166.42 (COOtBu), 204.38 (C3).

$[\alpha]_D^{26}$=−40.5 (c=1.15, $CHCl_3$)

A comparison of the specific rotation of the product from the enzymatic reduction with the literature value for the enantiomer-pure product shows that the present reaction yields an (R)-configured product with extremely high optical purity (literature: $[\alpha]_D^{26}$=−39.6 (c=2, $CHCl_3$), 99% ee (P. F. Deschenaux, T. Kallimopoulos, H. S. Evans, A. Jacot-Guillarmod, *Helv. Chim. Acta* 1989, 72, 731–737).

c)(3R, 5R)-Dihydroxy hexanoic acid-1,1-dimethyl Ethyl Ester

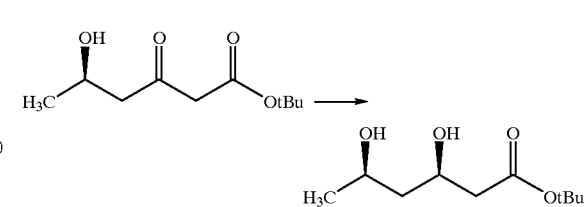

Starting with the (R)-5-hydroxy-3-oxohexanoic acid-1,1-dimethyl ethyl ester produced in step b), the desired target compound can be prepared by means of reduction with sodium boron hydride in the presence of diethyl methoxyborane. This process is described in the literature specifically for the application example at hand here (C. Masoni, P. F. Deschenaux, T. Kallimopoulos, A. Jacot-Guillarmod, *Helv. Chim. Acta* 1989, 72, 1284–128).

What is claimed is:

1. A method for the enantioselective reduction of 3,5-dioxocarboxylic acids, their salts and their esters having the Formula 4,

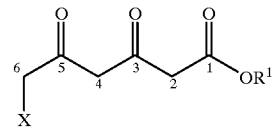

Formula 4 wherein
$R^1$ is alkyl, alkenyl, cycloalkyl, cycloalkenyl, aryl, aralkyl, cycloalkylalkyl, hydrogen or metal cation,
X is hydrogen, halogen, alkyl, aryl, CH=$CHR^2$, C≡$CR^3$,
$R^2$ is alkyl, alkenyl, cycloalkyl, cycloalkenyl, aryl, aralkyl, cycloalkylalkyl or hydrogen;
$R^3$ is alkyl, alkenyl, cycloalkyl, cycloalkenyl, aryl, aralkyl, cycloalkylalkyl, hydrogen or metal cation,
which comprises a reduction is catalyzed by means of an alcohol dehydrogenase in the presence of a co-factor.

2. The method according to claim 1, wherein said alcohol dehydrogenase is recombinant.

3. The method according to claim 1, wherein said alcohol dehydrogenase stems from Lactobacillus.

4. The method according to claim 3, wherein said alcohol dehydrogenase stems from *Lactobacillus brevis*.

5. The method according to claim 1, wherein said alcohol dehydrogenase is over-expressed in *Escherichia coli*.

6. The method according to claim 1, wherein X is fluorine or chlorine.

7. The method according to claim 1, wherein the radical $R^1$ is methyl, ethyl, n-propyl, i-propyl, allyl, t-butyl, pentyl, i-pentyl, n-hexyl, i-hexyl, vinyl, 1-propenyl, butenyl, i-butenyl, cyclopropyl, cyclobutyl, cyclopentyl, cyclohexyl, cycloheptyl, cyclopentenyl, cyclohexenyl, cycloheptenyl, cyclooctenyl, phenyl, p-tolyl, furanyl or benzyl.

8. The method according to claim 1, wherein the method is carried out at room temperature.

9. The method according to claim 1, wherein the method is carried out at a pH value of 5.5.

10. The method according to claim 1, wherein the reaction product in position 3 is reduced in a highly diastereoselective manner to form a syn-diol or an anti-diol.

11. The method according to claim 10, wherein the diastereoselective reduction is done by means of an enzyme.

12. The method according to claim 1, wherein the method is carried out in an enzyme membrane reactor.

13. The method according to claim 1, wherein the compounds according to Formula 4 are prepared by acylating dilithio-bisenolates according to Formula A

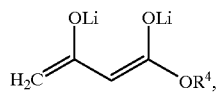
(A)

wherein $R^4$ is alkyl, alkenyl, cycloalkyl, cycloalkenyl, aryl, aralkyl, cycloalkyl, alkyl or metal cation, with carboxylic aced esters according to Formula B

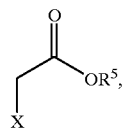
(B)

wherein $R^5$ is alkyl.

14. The method according to claim 13, wherein the method is carried out at a temperature between −97.6° F. and −85° F.

15. The method according to claim 13, wherein the method is cared out in an aprotic and coordinating solvent.

16. The method according to claim 14, wherein the method is cared out in an aprotic and coordinating solvent.

* * * * *

UNITED STATES PATENT AND TRADEMARK OFFICE
CERTIFICATE OF CORRECTION

PATENT NO. : 6,399,339 B1
DATED : June 4, 2002
INVENTOR(S) : Wolberg et al.

It is certified that error appears in the above-identified patent and that said Letters Patent is hereby corrected as shown below:

<u>Column 13,</u>
Line 20, delete "aced" and insert -- acid --.

<u>Column 14,</u>
Line 16, delete "cared" and insert -- carried --.

Signed and Sealed this

Eighth Day of October, 2002

Attest:

Attesting Officer

JAMES E. ROGAN
Director of the United States Patent and Trademark Office